US00PP13263P3

(12) United States Plant Patent
Vandenberg

(10) Patent No.: US PP13,263 P3
(45) Date of Patent: Nov. 19, 2002

(54) ROSE PLANT NAMED 'YOPILIT'

(75) Inventor: Cornelis P. Vandenberg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/821,997

(22) Filed: Mar. 31, 2001

(65) Prior Publication Data

US 2002/0144316 P1 Oct. 3, 2002

(51) Int. Cl.[7] ..... A01H 5/00

(52) U.S. Cl. ..... Plt./137

(58) Field of Search ..... Plt./137, 130, 136

*Primary Examiner*—Bruce R. Campell
*Assistant Examiner*—June Hwu
(74) *Attorney, Agent, or Firm*—C. A. Whealy

(57) ABSTRACT

A distinctive cultivar of Hybrid Tea Rose plant named 'Yopilit', characterized by its glossy dark green leaves; long, thick and green stems; large light pink-colored flowers; and good postproduction longevity.

1 Drawing Sheet

BOTANICAL CLASSIFICATION/CULTIVAR DESIGNATION

*Rosa hybrida* cultivar Yopilit.

BACKGROUND OF THE INVENTION

The present invention relates to a new and distinct cultivar of Hybrid Tea Rose plant, botanically known as *Rosa hybrida,* commercially produced as a cut flower, and hereinafter referred to by the name 'Yopilit'.

The new cultivar is a product of a planned breeding program conducted by the Inventor in Salinas, Calif. The objective of the breeding program was to develop new cut Rose cultivars with attractive flower petal colors, long and strong stems, dark green leaves and good postproduction longevity.

The new cultivar originated from a cross made by the Inventor in 1996 of the cultivar Matty, not patented, as the female, or seed, parent with the cultivar Madame Meilland, not patented, as the male, or pollen, parent. The cultivar Yopilit was discovered and selected by the Inventor as a flowering plant within the progeny of the stated cross in a controlled environment in June, 1998, in Madrid, Cundinamarca, Colombia.

Since December, 1998, asexual reproduction of the new cultivar by grafting on *Rosa Manetti* rootstocks in Madrid, Cundinamarca, Colombia, has shown that the unique features of the new cultivar are stable and reproduced true to type in successive generations of asexual reproduction.

SUMMARY OF THE INVENTION

The following traits have been repeatedly observed and are determined to be the unique characteristics of 'Yopilit'. These characteristics in combination distinguish the new Hybrid Tea Rose as a new and distinct cultivar:

1. Glossy dark green leaves.
2. Long, thick and green stems.
3. Large light pink-colored flowers.
4. Good postproduction longevity.

Plants of the Hybrid Tea Rose can be compared to plants of the female parent, the cultivar Matty. In side-by-side comparisons conducted by the Inventor in Salinas, Calif., plants of the new cultivar differed from plants of the cultivar Matty in the following characteristics:

1. Flowering stems of the new Hybrid Tea Rose have more thorns than flowering stems of the cultivar Matty.
2. Plants of the new Hybrid Tea Rose have lighter pink-colored flower petals than plants of the cultivar Matty.

Plants of the Hybrid Tea Rose can be compared to plants of the female parent, the cultivar Madame Meilland. In side-by-side comparisons conducted by the Inventor in Salinas, Calif., plants of the new cultivar differed from plants of the cultivar Madame Meilland in the following characteristics:

1. Plants of the new Hybrid Tea Rose have much longer flowering stems than plants of the cultivar Madame Meilland.
2. Flowering stems of the new Hybrid Tea Rose have more thorns than flowering stems of the cultivar Madame Meilland.
3. Plants of the new Hybrid Tea Rose have lighter pink-colored plower petals than plants of the cultivar Madame Meilland.

Plants of the new Hybrid Tea Rose have not been observed under all possible environmental conditions. The phenotype may vary significantly with variations in environment such as temperature, light, water status and/or fertilizer type and rate, without, however, any variance in genotype.

BRIEF DESCRIPTION OF PHOTOGRAPH

The accompanying colored photograph illustrates the new Hybrid Tea Rose plant, showing the colors as true as it is reasonably possible to obtain in colored reproductions of this type. Colors in the photograph may differ slightly from the color values cited in the detailed botanical description which accurately describe the colors of the new Hybrid Tea Rose.

The photograph comprises a side perspective view of a typical flowering stem of the new Hybrid Tea Rose grown in Midrid, Cundinamarca, Colombia.

DETAILED BOTANICAL DESCRIPTION

The following observations and measurements describe cut flowering stems of plants grown in Madrid, Cundinamarca, Colombia, in polyethylene-covered greenhouses with day temperatures ranging from 14 to 20° C., night temperatures ranging from 4 to 8° C., and light levels ranging from 3,000 to 5,000 foot-candles. Flowering stems used in the photograph and the description were about 78 days old. In the following description, color references are made to The Royal Horticultural Society Colour Chart except where general terms of ordinary dictionary significance are used.

Classification:

*Botanical.*—*Rosa hybrida* cultivar Yopilit.

*Commercial.*—Hybrid Tea Rose used as a cut flower.

Parentage:

*Female, or seed, parent.*—*Rosa hybrida* cultivar Matty, not patented.

*Male, or pollen, parent.*—*Rosa hybrida* cultivar Madame Meilland, not patented.

Propagation:

*Type.*—Cuttings grafted onto *Rosa Manetti* rootstocks.

Plant description:

*Form.*—Upright; narrow.

*Growth habit.*—Moderately vigorous.

*Plant height.*—About 76 to 91 cm.

*Plant width.*—About 20 cm.

*Stem and lateral branches (peduncles).*—Lateral branch length: About 76 to 91 cm. Lateral branch diameter: Base: Thick, about 8.5 mm. Apex: Thick, about 6 mm. Internode length: About 6.7 cm. Texture: Smooth. Strength: Strong. Color: Young and mature, close to 146A. Thorns: Quantity: Very thorny, about 21 per 12 cm of stem. Height: About 7 mm. Width at base: About 7 mm. Shape: Deltoid. Color, immature and mature: 59A.

*Foliage description.*—Arrangement: Alternate, compound with typically three to seven leaflets per leaf. Leaf length, five-leaflet leaves: Terminal leaves: About 8.8 cm. Lateral leaves: About 7.6 cm. Leaf width, five-leaflet leaves: Terminal leaves: About 5.3 cm. Lateral leaves: About 4.3 cm. Leaflet shape: Ovate. Leaflet apex: Acuminate. Leaflet base: Obtuse. Leaflet margin: Sharply serrate. Leaflet texture: Smooth, leathery, glabrous. Occasional small thorns on lower petiole and midrib of terminal leaflet, about 1.5 by 1.5 mm in size and close to 59A in color. Petiole length, 5-leaflet leaves: About 8.9 cm. Petiole diameter: At stem attachment: About 7 mm. At base of terminal leaves: About 1.5 mm. Stipules: Quantity: Two at base of petiole. Length: About 2 cm. Length of appendages: About 7 mm. Width: About 3 mm. Color: Young foliage, upper surface: Darker than 147A, glossy. Young foliage, lower surface: Close to 147B. Mature foliage, upper surface: Much darker than 147A, glossy; venation, 147A. Mature foliage, lower surface: Close to 147B; venation, 146B to 146C. Petiole: Upper surface: 187A. Lower surface: 146A, nodes, 187A. Stipules, upper surface: Much darker than 147A. Stipules, lower surface: Close to 147B.

Flower description:

*Flower type and habit.*—Large light pink-colored flowers. Consistently symmetrical rosette flowers. Freely and recurrent flowering. Flowers arranged singly at terminal apices. Flowers persistent.

*Flowering season/time to flower.*—Year-round under greenhouse conditions. Depending on environmental conditions and season, time to flower is about 70 days.

*Flower diameter, fully opened.*—About 12 cm.

*Flower depth (height), fully opened.*—About 5.3 cm.

*Flower longevity as a cut flower.*—At least 7 to 10 days.

*Fragrance.*—Slight, typical Hybrid Tea Rose fragrance.

*Flower buds.*—Shape: Ovoid. Length: About 5.1 cm. Color: 144A.

*Petals and petaloids.*—Petaloids vary in size, but similar to petals in shape and coloration. Quantity: About 38. Length, outer petals: About 6.3 cm. Width, outer petals: About 6.7 cm. Shape: Obovate. Apex: Mostly rounded with small point. Base: Obtuse. Margin: Mostly entire, slightly emarginate. Texture: Smooth, satiny. Color: When opening, upper surface: Center and towards base, 155A, and center towards margin, 63A to 63D. When opening, lower surface: Center and towards base, 155A, and center towards margin, 63A to 63D. Fully opened, upper surface: Center and towards base, 155A, and center towards margin, 63B, fading to 63C with subsequent development. Fully opened, lower surface: Center and towards base, 155A to close to 19D, and center towards margin, 63C.

*Sepals.*—Quantity: Five. Length: About 6.2 cm. Diameter: About 1.2 cm. Shape: Sharply lanceolate. Apex: Elongated, acuminate. Base: Fused at receptacle. Margin: Cilate with occasional sharply acuminate appendages. Texture: Upper surface, pubescent; lower surface, glabrous. Color: Upper surface: Closest to 144B. Lower surface: 144A with central anthocyanin stripe, 59A.

*Reproductive organs.*—Stamens: Quantity: About 112 per flower. Anther length: About 3 mm. Anther diameter: About 2 mm. Anther shape: Cordate, concave. Anther color: Close to 17A. Filament length: About 3 mm. Filament color: Close to 58D. Pollen amount: None. Pistils: Quantity: About 34 per flower. Pistil length: About 1.1 cm. Style color: 45A. Stigma shape: Bi-lobed. Stigma color: Close to 5C. Ovary color: 145D to 155D. Receptacle height: About 1.9 cm. Receptacle diameter: About 1.5 cm. Receptacle texture: Smooth. Receptacle color: 144A to 146A.

*Seed.*—None observed.

Disease resistance: Plants of the new Hybrid Tea Rose have been observed to be somewhat resistant to Powdery Mildew.

It is claimed:

1. A new and distinct Hybrid Tea Rose plant named 'Yopilit', as illustrated and described.

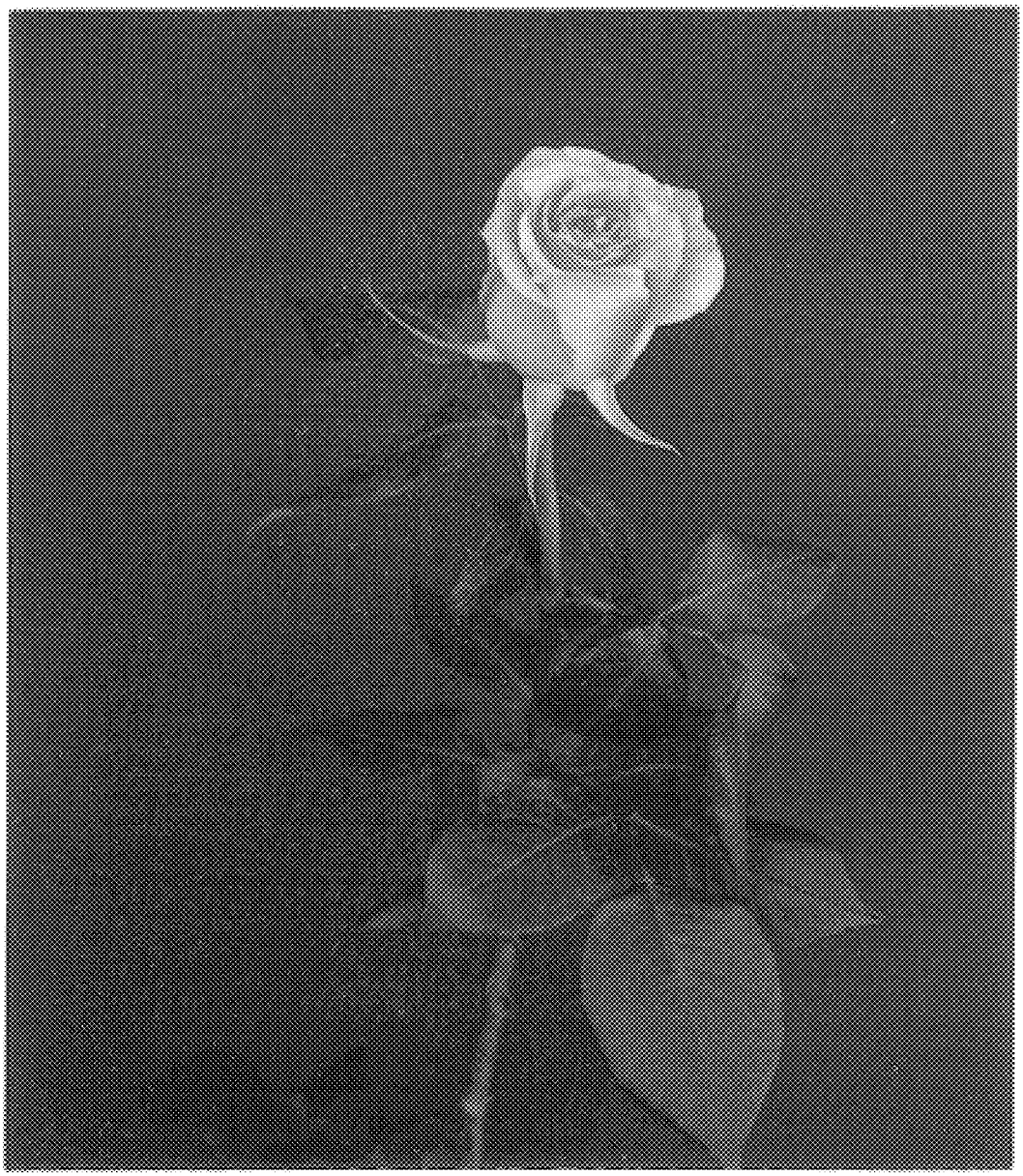

* * * * *